United States Patent [19]

Doyle

[11] Patent Number: 4,812,041

[45] Date of Patent: Mar. 14, 1989

[54] SPECTROMETER SYSTEM HAVING PIVOTALLY MOUNTED INTERNAL REFLECTANCE ELEMENT

[75] Inventor: Walter M. Doyle, Laguna Beach, Calif.

[73] Assignee: Laser Precision Corporation, Irvine, Calif.

[21] Appl. No.: 161,007

[22] Filed: Feb. 26, 1988

[51] Int. Cl.⁴ ............................ G01B 9/02; G01J 3/45
[52] U.S. Cl. .................................... 356/346; 356/440; 356/244
[58] Field of Search ................ 356/244, 300, 346, 440

[56] References Cited

U.S. PATENT DOCUMENTS

| | | | |
|---|---|---|---|
| 3,393,603 | 7/1968 | Harrick | 356/246 |
| 4,591,266 | 5/1986 | Doyle | 356/244 |
| 4,657,390 | 4/1987 | Doyle | 356/244 X |

FOREIGN PATENT DOCUMENTS 2030323 1/1971 Fed. Rep. of Germany .

OTHER PUBLICATIONS

Harrick, "Multiple Reflection Cells for Internal Reflection Spectrometry" *Analytical Chemistry*, vol. 36, No. 1 pp. 188–191, 1/64.

Harrick, "Nanosampling Via Internal Reflection Spectroscopy", *Applied Spectroscopy*, vol. 41, No. 1, pp. 1–2, 1/87.

Primary Examiner—Davis L. Willis
Assistant Examiner—Matthew W. Koren
Attorney, Agent, or Firm—Thomas J. Plante

[57] ABSTRACT

A spectrometer system is disclosed in which a single ended internal reflectance element (IRE) is readily insertable into, and removable from, liquid samples being analyzed. The IRE is carried by an articulated housing construction having enclosed radiation passages, through which radiation is directed by a plurality of mirrors. The IRE-supporting enclosure is pivotally mounted by means of aligned rotatable members, which permit the IRE to be moved into and out of samples without disconnecting or re-purging the enclosed radiation passages.

8 Claims, 7 Drawing Sheets

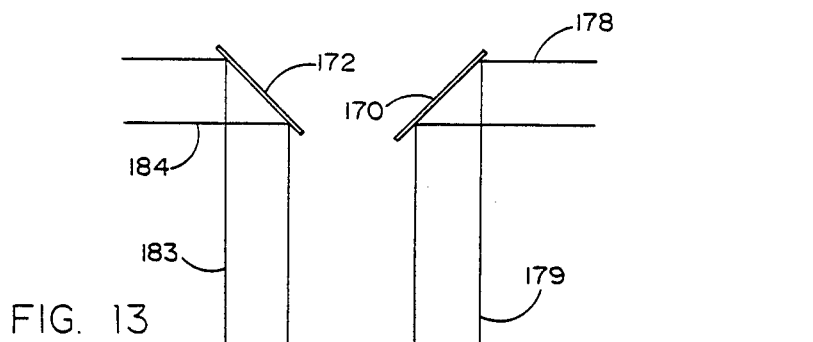
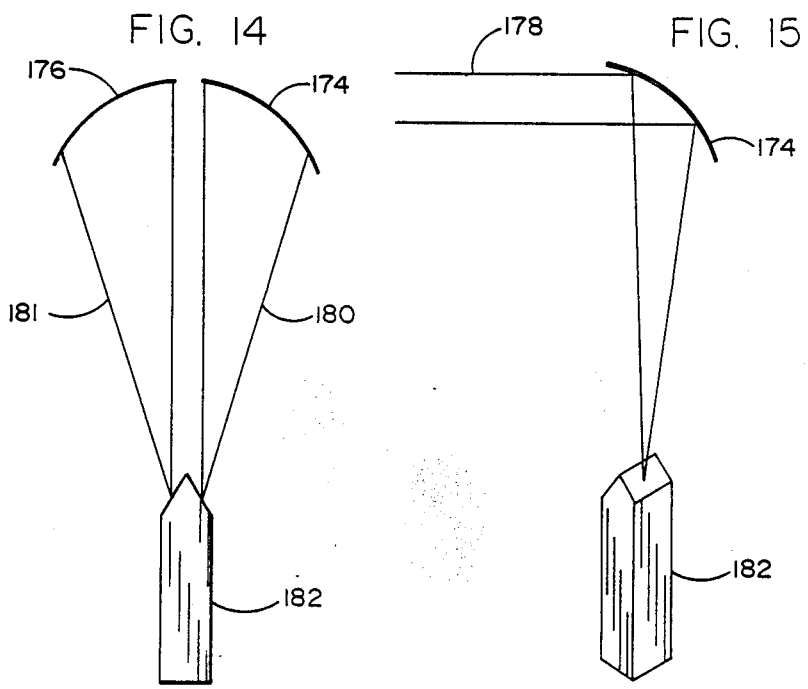

SPECTROMETER SYSTEM HAVING PIVOTALLY MOUNTED INTERNAL REFLECTANCE ELEMENT

BACKGROUND OF THE INVENTION

This invention relates to the field of spectrometry, and to that type of sample analysis in which an internal reflection element is immersed in a sample, usually a liquid material.

As discussed in a copending application having the same inventor and, the same assignee as this application (Ser. No. 158,214 filed 2/19/88), an accessory referred to as a "prism liquid cell" is marketed by Harrick Scientific Corporation. This accessory is used to replace "amalgamated sealed cells," which were previously used to hold sample material, through which previously used to hold sample material, through which radiation was passed to provide transmission spectroscopy.

In internal reflection spectroscopy by an accessory extending into the sample material, an internally reflecting element (IRE) is surrounded by the sample; and the analytical radiation is essentially confined inside the IRE. Infrared light may enter and leave the IRE from the same end, which may have the shape of a 90° rooftop. The Harrick accessory is a rectangular cross-section crystal (typically composed of zinc selenide) having its outer (non-immersed) end cut at an angle of 45° to each of its long sides.

Infrared light from a source enters the first inclined side of the rooftop, generally on a perpendicular path. The infrared light is reflected first from one wall of the IRE, then from the opposite wall of the IRE, and so on, until it reaches the end of the IRE. It is then returned, along a path parallel to the incoming radiation, by reflection back and forth across the IRE until it exits the IRE from the second inclined side of the rooftop. And it is then directed to an infrared detector.

If the IRE (also referred to as a prism or crystal) is surrounded by air, the internal radiation from the source will be totally reflected. However, if the IRE is in contact with an infrared absorbing material, such as a liquid chemical, the radiation will be selectively absorbed at various wavelengths, resulting in an infrared spectrum. The amount of radiation absorbed is influenced by the angle of the incidence of the radiation on the sides of the IRE.

IREs are often referred to as attenuated total reflectance (ATR) crystals, because the internal reflectance permits a limited amount of light absorption by the sample surrounding the crystal. The angle of incidence of the internal light on the crystal walls must be at or above the critical angle. If the angle of incidence is too small, excessive radiation will leave the crystal and be absorbed by the sample. If the angle of incidence is too large, excessive radiation will be internally reflected, and insufficient radiation will be absorbed by the sample to provide adequate analytical information. In other words, sample absorption of radiation is necessary, but sufficient radiation must return and exit from the crystal on its way to the detector.

A thrust of certain applications assigned to the assignee of the present application is the development of spectrometer systems, and components thereof, which are readily adaptable to different uses, and to uses with different samples. For example, application Ser. No. 900,730, filed Aug. 27, 1986, provides a spectrometer system using components which are both modular and switchable. The switchability provides the versatility of having a number of interconnected units which give the convenience of ready access, while the modularity permits easy and time-saving re-structuring of the accessory combination included in the system.

SUMMARY OF THE INVENTION

The present invention provides several embodiments of an articulated supporting structure which carries an internal reflectance element (IRE), and which permits the position of the IRE to be easily rotated to immerse the IRE in a sample, remove the IRE from a sample, and clean it between samples, with total isolation between sample and optics. Because of this isolation, there is no need to break purge when changing samples or cleaning the IRE, and there is no risk of sample-caused damage to the spectrometer.

Except for the portion of the IRE which is lowered into the sample, the optical elements are sealed inside a hollow enclosure. The enclosure may comprise an IRE-supporting tube-like member connected at each end to a hollow tube-like arm. Each arm contains radiation-directing mirrors, and each arm is rotatable about a pivot point located at some distance from the IRE-supporting enclosure. A first rotary member connects the pivoted end of one arm to a radiation path leading to a source of pre-sample infrared radiation. And a second rotary member connects the pivoted end of the other arm to a radiation path leading to a detector of post-sample infrared radiation.

BRIEF DESCRIPTION OF THE DRAWINGS

FIGS. 13 and 14 show top and side views, respectively, of the optical elements of an embodiment similar FIG. 15 is an isometric showing the relationship of the IRE roof of FIGS. 13 and 14 to the aspheric mirror located directly above the IRE.

BRIEF DESCRIPTION OF SPECIFIC EMBODIMENTS

Figure 2:
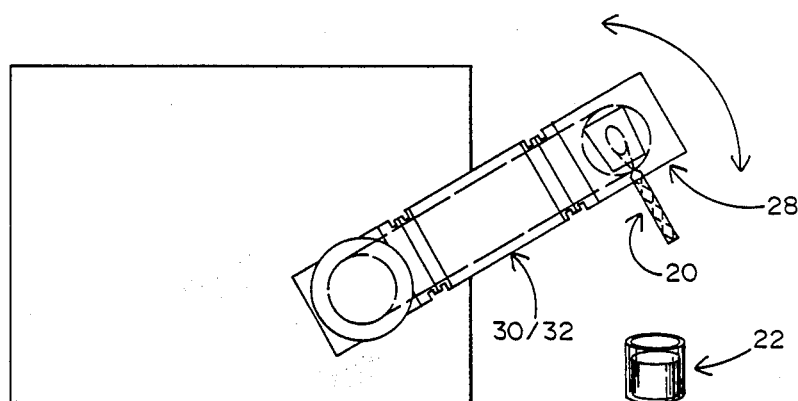
FIG. 2 is a view in a vertical plane, showing an articulated unit in which the IRE has been rotated into the sample-changing position.

As seen in FIG. 2, performance of an analytical experiment, in the context of this invention, requires immersing a single ended IRE (internal reflectance element) 20 into a container (beaker) 22, which has an amount of sample material, usually a liquid. In order to change from one sample to the next, it is necessary to remove the IRE 20 from the sample, clean the IRE, and then immerse the IRE in another sample. As shown in FIG. 2, this is readily accomplished by tilting upwardly the structure from which the IRE protrudes.

Figure 1:
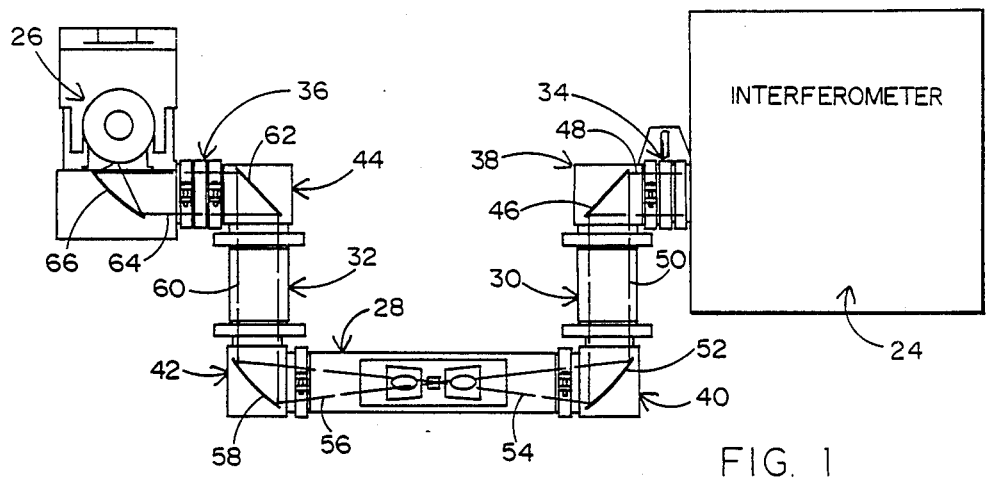
FIG. 1 is a plan view showing diagrammatically a spectrometer system incorporating the present invention.

FIG. 1 shows a spectrometer system incorporating the articulated structure which supports the IRE, and through which source-provided pre-sample analytical radiation travels into the IRE, and post-sample radiation travels out of the IRE to a detector. An interferometer 24 provides the pre-sample analytical radiation, and a detector 26 receives the post-sample analytical radiation.

As shown (FIG. 3), the IRE 20 protrudes from a hollow elongated enclosure 28, one end of which is connected at right angles (FIG. 1) to a hollow enclosure, or arm, 30 leading to interferometer 24, and the other end of which is connected at right angles to a hollow enclosure, or arm, 32 leading to detector 26. The sub-assembly which comprises the three enclosures 28, 30 and 32 is rotatable as a unit about a center provided by aligned rotary members 34 and 36 connected, respectively, to the interferometer 24 and to the detector 26. Because the hollow enclosures 28, 30 and 32 are essentially enclosed passages, it is convenient to refer to them as tubes, even though their preferred cross-sectional shape is square (rather than cylindrical). This preference has to do primarily with manufacturing, rather than functional, considerations.

Four enclosure elements 38, 40, 42 and 44, conveniently referred to as corner tubes, provide interconnecting passages in which the infrared radiation is redirected at right angles as it travels from the interferometer 24 to the detector 26. The corner tube 38 encloses a flat mirror 46, which is positioned at a 45° angle to a collimated interferometer output beam traveling along path 48, and which redirects that collimated beam along path 50. The corner tube 40 encloses a parabolic mirror 52 which reflects collimated beam 50 as a converging beam 54. Beam 54 is directed into the sample-immersed IRE 20, as described in detail below. A diverging beam 56, returning from the IRE 20, is reflected by a parabolic mirror 58, which is enclosed in the corner tube 42. After reflection by mirror 58, the beam is a collimated beam traveling along path 60. It is reflected at right angles by a flat mirror 62, which is enclosed in the corner tube 44, and thereafter travels as a collimated beam along path 64, until it is reflected by a short focal length parabolic mirror 66 and caused to focus at detector 26.

Figure 3:
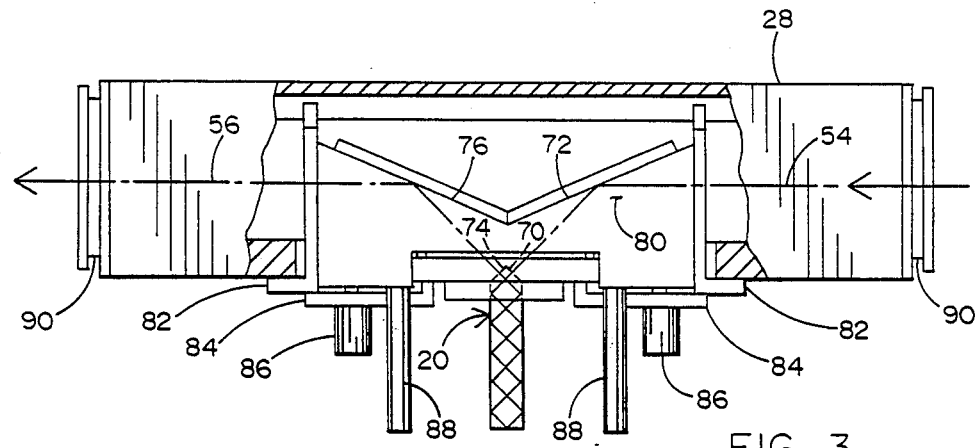
FIG. 3 is an elevation view, partly in cross-section, showing the portion of the FIG. 1 system in which a sealed elongated mirror enclosure, or housing, is combined with a protruding IRE adapted to be immersed in a liquid container.
Figure 4:
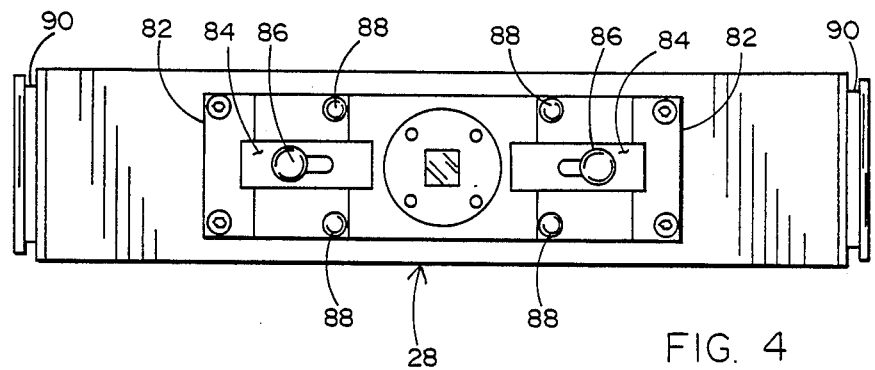
FIGS. 4 and 5 are bottom and end views, respectively, of the combined mirror housing and protruding IRE of FIG. 3.
Figure 5:
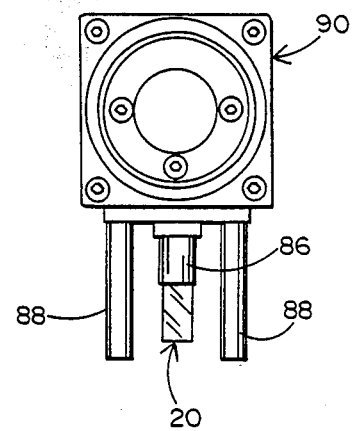

FIGS. 3 and 4 show details of the IRE sub-assembly which is carried by elongated tube 28. The IRE 20, usually referred to as an attenuated total reflectance (ATR) crystal, is retained in position by a mechanical structure secured to tube 28. The upper end of the IRE is shaped like a roof top having two flat surfaces which are inclined from the center down to the sides at equal angles from the vertical. One of the inclined surfaces 70 is the radiation entering surface, through which incoming infrared radiation beam 54 enters the IRE, after being reflected by a flat mirror 72. The other inclined surface 74 is the radiation exiting surface, through which infrared radiation emerges from the IRE, after attenuation by the sample, and becomes outgoing radiation beam 56, after being reflected by a flat mirror 76. (Converging pre-sample beam 54, and diverging post-sample beam 56, are illustrated symbolically by interrupted straight lines in FIG. 3).

The function of the IRE as a sample-analyzing element in a spectrometer has been discussed at length in the literature, and is also described in more detail in a copending, common assignee application (Ser. No. 158,214 filed 2/19/88).

Although the lower portion of the IRE 20 is immersed in the sample, its upper roof top surfaces are inside the tube 28, which is sealed in order to maintain "purge," i.e., to exclude atmosphere by keeping the optical system bathed in an inert gas, such as nitrogen, during the spectrometer experiments.

A mechanical sub-assembly, indicated generally by numeral 80, is inserted in, and secured to elongated tube 28. It provides support for mirrors 72 and 76, and for IRE 20. Sub-assembly 80 is held in position by two end plates 82, two clamps 84, and two thumb screws 86. Projecting downwardly from sub-assembly 80, in addition to the IRE, are four legs 88 which rest on a sample-supporting platform when the IRE is in its sample-immersed position.

Figure 6:
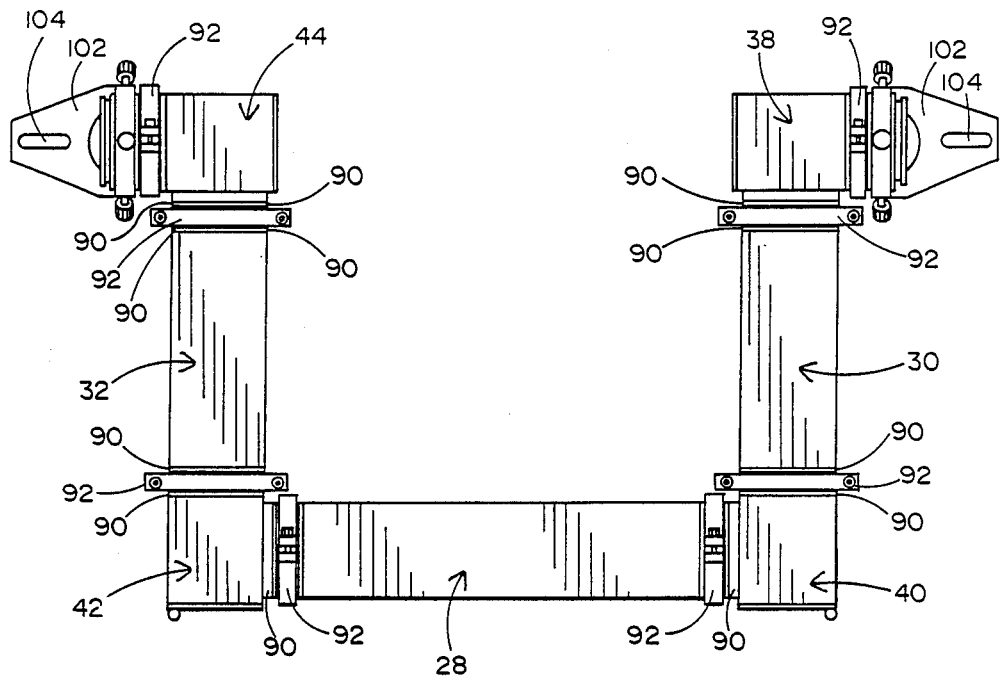
FIG. 6 is a top exterior view of an articulated optical system incorporating the structure of FIGS. 3-5.
Figure 7:
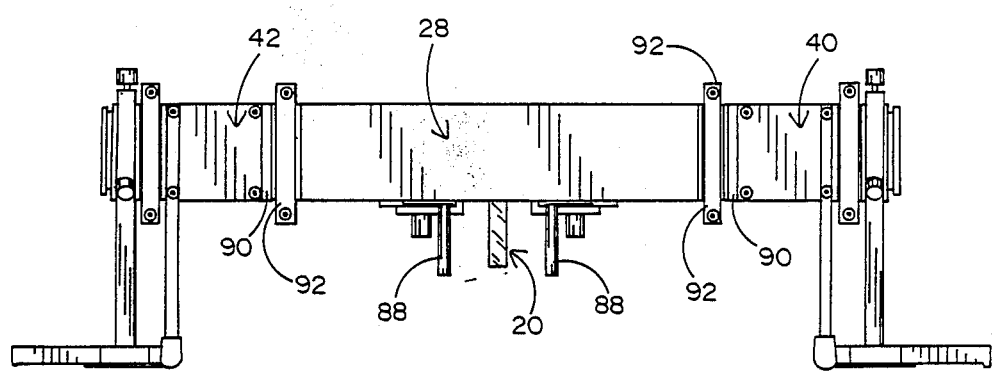
FIG. 7 is a side exterior view of the articulated optical system of FIG. 6.

Interconnection of the enclosures, or tubes, 28, 30, 32, 38, 40, 42 and 44 is preferably accomplished by modular interface elements similar to those described in common assignee application Ser. No. 900,730, filed Aug. 27, 1986. As shown in FIGS. 3 and 4, elongated tube 28 has an interface element 90 secured to each of its ends. As seen in FIGS. 6 and 7, each of the corner tubes 40 and 42 has two interface elements 90 secured thereto, one at each of its open ends. The interface elements 90 of two adjacent tubes engage one another, and are secured in their interengaged relationship by an exterior clamping device 92. In FIGS. 6 and 7, the interconnections between the tubes 28, 40 and 42 are rigid in each instance.

However, the connection between corner tube 38 and interferometer 24, and the connection between corner tube 44 and detector 26, each incorporate a member which permits rotation of the tube assembly as a whole, in order to permit the user to raise and lower the IRE 20. These rotary connections 34 and 36 (FIG. 1) permit the rotary motion desired without obstructing the internal radiation path.

Figures 8, 9:
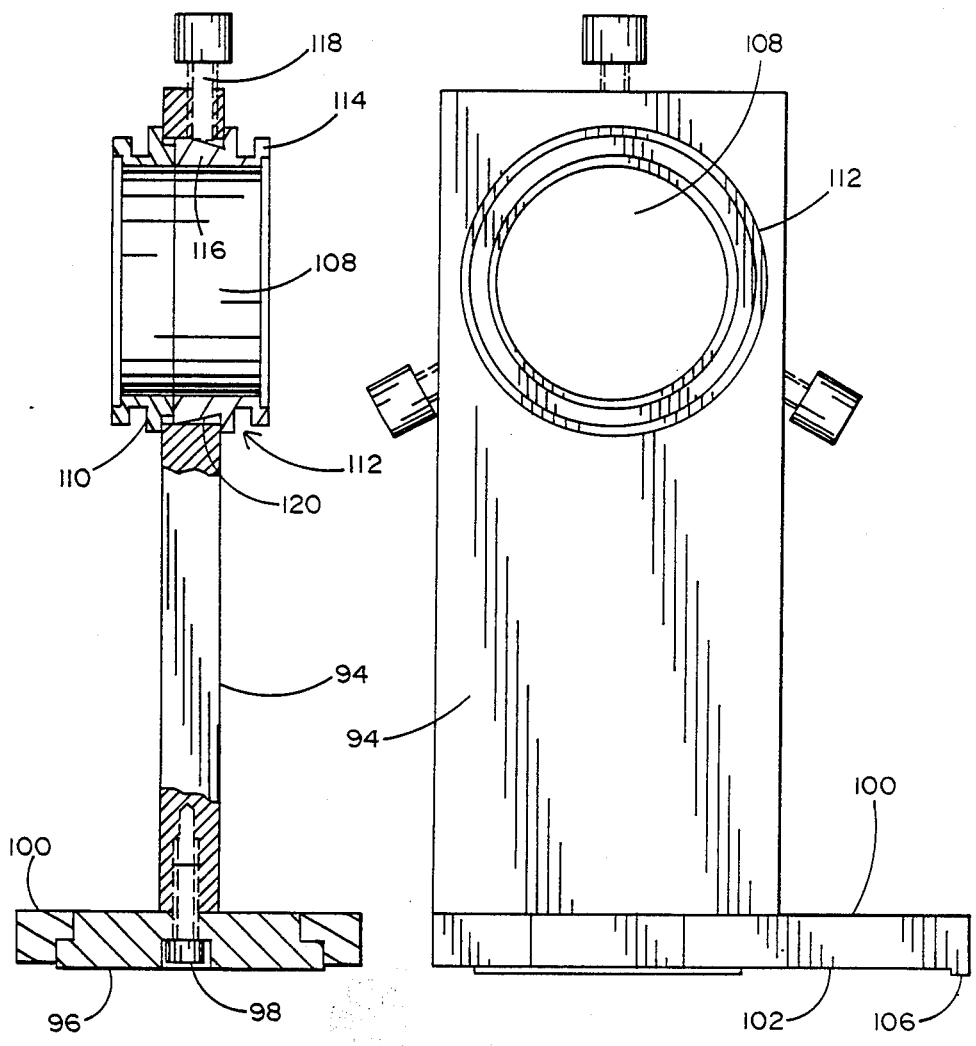
FIG. 8 is an elevation view showing a pivot support which carries one of the articulated joints of FIG. 6.
FIG. 9 is a cross-section in a vertical plane taken through the pivot support of FIG. 8.

As seen in FIGS. 8 and 9, each of the two rotary connections may be provided by a pivot support sub-assembly comprising a vertically extending plate 94 secured to a base member 96 by a cap screw 98 extending upwardly into plate 94. Base member 96 is held in place by a clamp member 100, which has an integral arm 102 extending laterally to provide a slot 104 (FIG. 6), through which a fastener (not shown) extends to secure the clamp member 100 to a supporting platform. A downwardly projecting nib 106 in arm 102 is adapted to enter a recess in the supporting platform to prevent movement of clamp member 100. The position of vertical plate 94 may be adjusted for alignment purposes.

A circular opening 108 extends through vertical plate 94 near its upper end. Secured in one side of opening 108 is an interface element 110, which is adapted to be secured to an interface element on the adjacent interferometer or detector housing.

A pivot ring 112, which provides the rotary element of the joint, extends into the other side of opening 108 in plate 94. Pivot ring 112 has a flange 114 which engages the interface element 90 on the adjacent corner tube 38 or 44, and is clamped thereto by a clamp 92 (FIG. 6). The portion 16 of pivot ring 112 which is inside circular opening 108 is rotatable with respect to plate 94, if it is not locked in position by a thumbscrew 118. The outer surface of pivot ring 112 is preferably tapered, as shown at 120, so that tightening of thumbscrew 118 not only prevents rotation of pivot ring 112, but also holds the pivot ring in tight engagement with the adjacent surface of interface element 110.

The purposes of the articulated (hinged) IRE-supporting structure could be accomplished by enclosing the mirrors 46, 52, 72, 76, 58 and 62 in a single housing. Such a housing, and the IRE, would still be pivotally movable by rotation around rotary members 34 and 36, which comprise annular pivot members 112.

Figure 10:
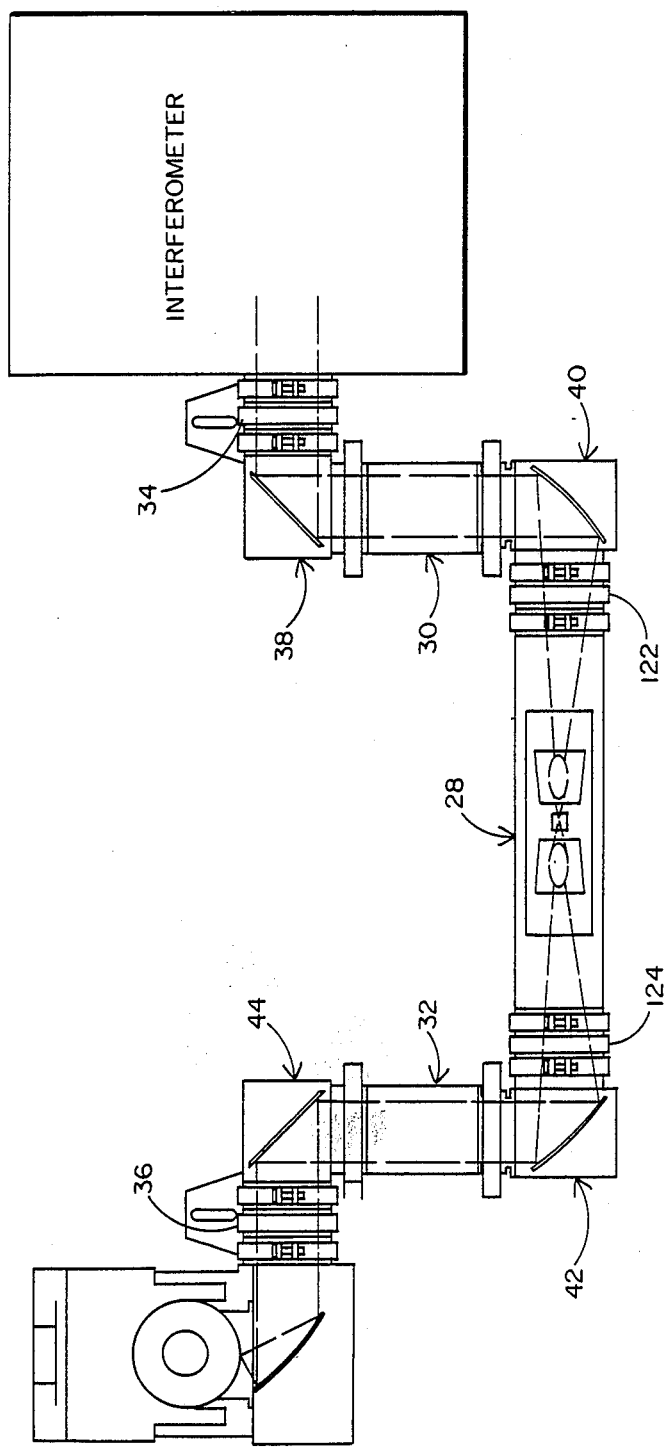
FIG. 10 is a plan view showing a spectrometer system which differs from that of FIG. 1 by providing additional points of articulation, in order to maintain the IRE in a substantially vertical position as it is moved into and out of a sample container.

FIG. 10 shows an articulated sub-assembly similar to that in FIG. 1, except that the FIG. 10 structure has two additional rotary members, so located that the IRE may remain in a vertical orientation as it is moved into and out of the sample. Between one end of tube 28 (which carries IRE 20) and the adjacent corner tube 40, an annular rotary member 122 is connected; and between the other end of tube 28 and the adjacent corner tube 42, an annular rotary member 124 is connected. During the raising and lowering of the IRE 20, both members 122 and 124 rotate, along with members 34 and 36 This permits the IRE to retain its vertical position, and thus to be moved into and out of smaller container opening than would otherwise be possible.

One of the limitations of the previous embodiments is the lack of vertical space available between the articulated sub-assembly and the sample-supporting platform. In other words, it is not possible to dip the IRE very deeply into a container, due to the proximity of the horizontal structure of the sub-assembly. In some instances, it is desirable to locate the primary optical elements at a greater vertical distance above the IRE. The remaining figures show embodiments which solve this problem.

Figure 12:
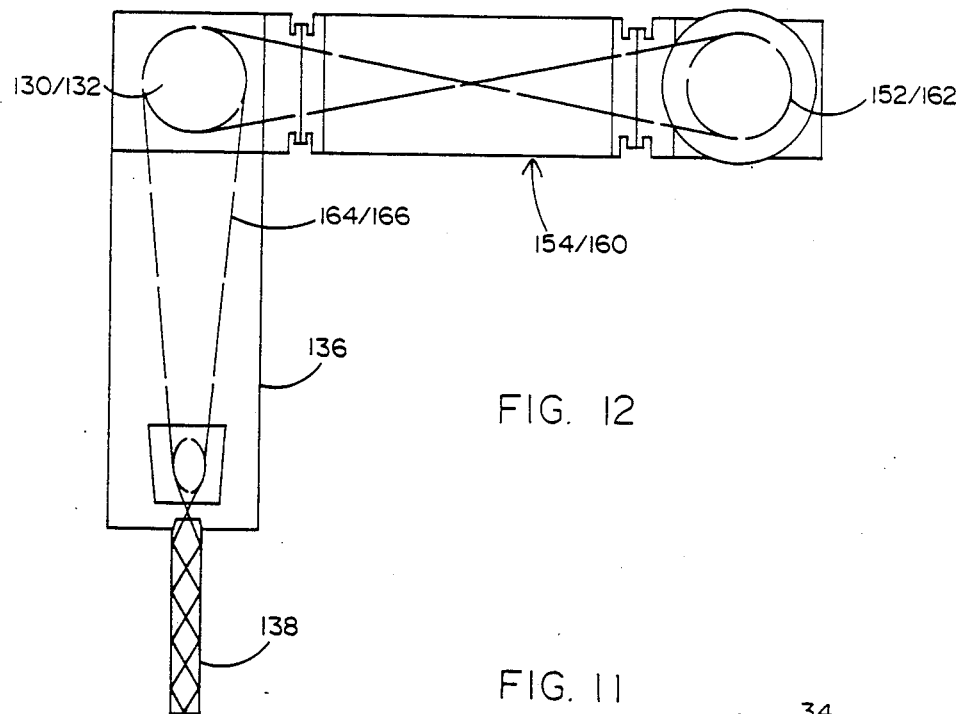
FIGS. 11 and 12 show top and side views, respectively, of an articulated IRE supporting structure, in which the IRE is capable of dipping more deeply into a sample container than is possible with the previous embodiments.
Figure 11:
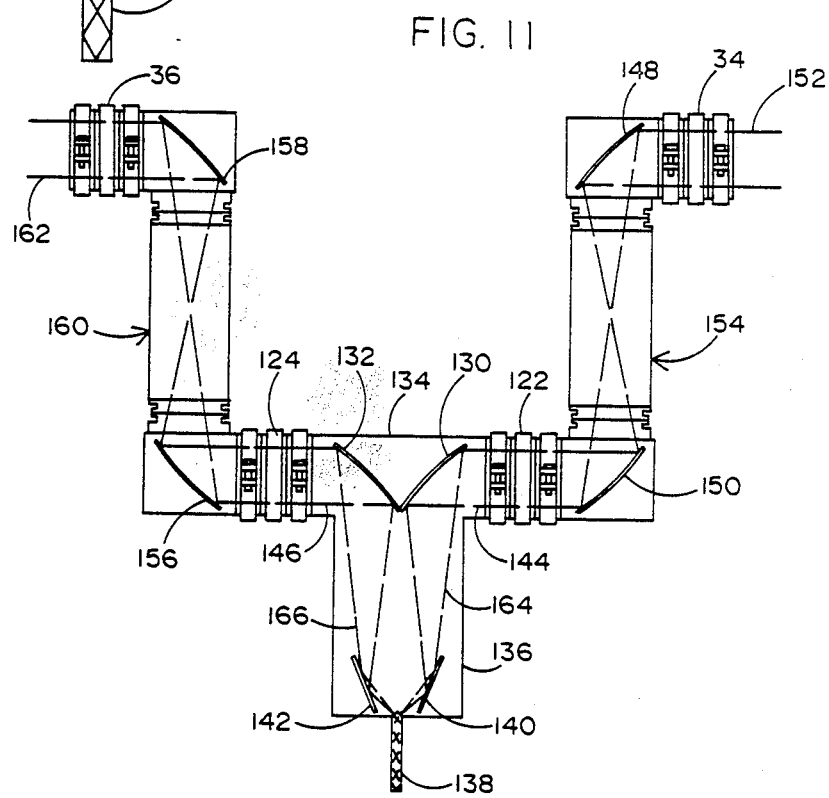

In the structure of FIGS. 11 and 12, instead of the flat mirrors 72 and 76 (FIG. 3), back to back parabolic reflectors 130 and 132 are mounted in an IRE-carrying tube 134; and another tube 136, carried by tube 134, extends in a perpendicular direction from tube 134. At the lower end of tube 136, a projecting IRE 138 is mounted. Two flat mirrors 140 and 142 are mounted inside tube 136 adjacent to the rooftop of IRE 138.

In order to provide collimated radiation beams 144 and 146 traveling, respectively, toward mirror 130 and away from mirror 132, one pair of confocal parabolic mirrors 148 and 150 are arranged to direct an incoming collimated beam 152 from the interferometer along one arm 154 of the articulated sub-assembly, and another pair of confocal parabolic mirrors 156 and 158 are arranged to direct radiation along the other arm 160 of the articulated sub-assembly and to provide a collimated beam 162 traveling toward the detector. The incorporation of the two pairs of confocal parabolic mirrors in the radiation paths into and out of IRE 138 provides the additional advantage of throughput conservation, as discussed in common assignee application Ser. No. 895,211, filed Aug. 11, 1986.

The articulated structure in FIGS. 11 and 12 includes the same pivoting rotary members 34, 36, 122 and 124 as the structure in FIG. 10. When the IRE 138 is in sample contact, tube 136 permits deeper immersion in the sample container. The immersed position is shown in FIG. 12, which is a side view. A converging beam 164 (FIG. 11) reflected downwardly by parabolic mirror 130, is then reflected by flat mirror 140 into the top of the IRE. Radiation returning from the IRE is reflected upwardly by flat mirror 142 as a beam 162, which is collected and collimated by parabolic mirror 132. Because the focal points of mirrors 130 and 132 are displaced some distance from horizontal tube 134, the IRE 138 (and tube 136) can be dipped more deeply into the sample. With this arrangement, the presence of the second pair of rotary joints 122 and 124 becomes more important than in the structure of FIG. 10.

FIGS. 13-15 show an embodiment which reduces the number of mirrors required. In these figures, only the radiation path is shown, not the tubular elements. Two flat mirrors 170 and 172, and two parabolic mirrors 174 and 176, are the only mirrors required. A collimated incoming beam 178 is reflected by flat mirror 170, and continues as a collimated beam 179 until it reaches parabolic mirror 174. Parabolic mirror 174 reflects the radiation as a converging beam 180 (FIGS. 14 and 15) which travels directly to the top of IRE element 182.

As the returning radiation comes from the IRE 182, it follows a diverging path 182 until it is collected and reflected by parabolic mirror 176. Thereafter a collimated beam 183 (FIG. 13) travels toward flat mirror 172, and is reflected as an outgoing collimated beam 184.

Because of the smaller distance between the pairs of mirrors in this embodiment, it lends itself readily to use of a single enclosure for the entire articulated sub-assembly. A limitation of this embodiment is the fact that only one pair of rotary joints can be used. In other words, only one axis of rotation is available, i.e., the axis of the aligned collimated beams 178 and 184.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. In a spectrometer system having an interferometer which provides pre-sample radiation and a detector which receives post-sample radiation, a structure for illuminating samples by immersing an optical element therein, comprising:

a single ended internal reflectance element (IRE) adapted to be immersed in a sample;

a hollow enclosure which supports the IRE with the top of the IRE inside the enclosure and the body of the IRE projecting outside the enclosure for immersion in a sample;

a first means for directing an entering radiation beam into the enclosure;

a second means for directing an exiting radiation beam out of the enclosure;

the entering and exiting radiation beams being aligned with one another; and means for pivotally mounting the enclosure to provide rotary movement of the enclosure around the aligned entering and exiting beams, in order to move the IRE into and out of a sample.

2. The spectrometer system of claim 1 in which the IRE-supporting hollow enclosure comprises:

a first tube extending parallel to the aligned incoming and outgoing beams;

a second tube connected to one end of the first tube;

a third tube connected to the other end of the first tube;

a first mirror for deflecting the incoming beam to cause it to travel through the second tube;

a second mirror for deflecting the beam from the second tube to cause it to travel through the first tube;

a third mirror for deflecting the beam from the first tube to cause it to travel through the third tube; and a fourth mirror for deflecting the beam from the third tube to provide the outgoing beam.

3. The spectrometer system of claim 2 which also comprises:

means for rotatably mounting the first tube with respect to the second and third tubes.

4. The spectrometer system f claim 1 which also comprises:

a first reflector in the hollow enclosure which is positioned above the IRE, and which reflects incoming radiation into the IRE; and a second reflector in the hollow enclosure which is positioned above the IRE, and which reflects outgoing radiation received from the IRE.

5. The spectrometer system of claim 4 in which the first and second reflectors are flat mirrors located near the top of the IRE.

6. The spectrometer system of claim 4 in which the first and second reflectors are parabolic mirrors located at a distance from the top of the IRE.

7. The spectrometer system of claim 6 which also comprises:

a tube carried by the hollow enclosure which extends downwardly therefrom, and which carries the IRE at its lower end.

8. In a spectrometer system having an interferometer which provides pre-sample radiation and a detector which receives post-sample radiation, a structure for illuminating samples by immersing an optical element therein, comprising:

a single ended internal reflectance element (IRE) adapted to be immersed in a sample;

a first hollow enclosure which supports the IRE with the top of the IRE inside the enclosure and the body of the IRE projecting outside the enclosure for immersion in a sample;

the first enclosure providing a passage for a pre-sample radiation beam entering the internal reflectance element and for a post-sample radiation beam leaving the internal reflectance element;

a second hollow enclosure communicating with the first enclosure and with the interferometer;

the second enclosure extending at an angle from one end of the first enclosure, and providing a passage for pre-sample radiation traveling from the interferometer toward the internal reflectance element;

a third hollow enclosure communicating with the first enclosure and with the detector;

the third enclosure extending at an angle from the other end of the first enclosure, and providing a passage for post-sample radiation traveling from the internal reflectance element toward the detector;

a first pivotal connection between the interferometer and the end of the second enclosure remote from the first enclosure;

a second pivotal connection between the detector and the end of the third enclosure remote from the first enclosure;

the first and second pivotal connections being rotatable about colinear axes in order to permit the interconnected first, second and third enclosures to be pivotally moved as a unit in such a way as to move the internal reflectance element into and out of immersion in the sample.

* * * * *